United States Patent [19]

Asano et al.

[11] 4,108,893

[45] Aug. 22, 1978

[54] PURIFICATION OF AN AQUEOUS SOLUTION OF ACRYLAMIDE

[75] Inventors: Shiro Asano; Kohei Shizuka, both of Mobara; Junji Mikami, Takaishi; Kenichi Hirakawa, Takaishi; Mutsuo Matsumura, Takaishi, all of Japan

[73] Assignee: Mitsui Toatsu Chemicals, Incorporated

[21] Appl. No.: 762,842

[22] Filed: Jan. 27, 1977

[30] Foreign Application Priority Data

Feb. 17, 1976 [JP] Japan ................... 51-15480

[51] Int. Cl.$^2$ .............................................. B01D 15/04
[52] U.S. Cl. .................. 260/561 N; 210/26; 210/37 B; 210/38 B
[58] Field of Search ............... 210/24, 26, 37 R, 37 B, 210/38 R, 38 B, 63 R; 260/561 N

[56] References Cited

U.S. PATENT DOCUMENTS

| | | | |
|---|---|---|---|
| 2,865,960 | 12/1958 | Shearer et al. | 260/561 N |
| 3,642,894 | 2/1972 | Habermann et al. | 260/561 N |
| 3,804,897 | 4/1974 | Haefele et al. | 260/561 N |
| 3,887,618 | 6/1975 | Hein | 260/561 N |
| 3,911,009 | 10/1975 | Yoshimura et al. | 260/561 N |
| 3,923,741 | 12/1975 | Asano et al. | 260/561 N |
| 3,941,837 | 3/1976 | Asano et al. | 260/561 N |
| 3,962,333 | 6/1976 | Yoshimura et al. | 260/561 N |

FOREIGN PATENT DOCUMENTS

| | | |
|---|---|---|
| 49-7,219 | 1/1974 | Japan. |
| 49-36,616 | 4/1974 | Japan. |
| 50-62,929 | 5/1975 | Japan. |
| 50-82,011 | 7/1975 | Japan. |
| 50-83,323 | 7/1975 | Japan. |

*Primary Examiner*—Frank A. Spear, Jr.
*Assistant Examiner*—Ivars Cintins

[57] ABSTRACT

An improved process is disclosed for the purification of an aqueous solution of acrylamide. It comprises bringing a crude aqueous solution of acrylamide into contact with oxygen or an oxygen-containing gas and thereafter subjecting the solution to a dual treatment with a strongly acidic cation exchange resin followed by a weakly basic anion exchange resin. If necessary, the aqueous solution of acrylamide is treated, while maintaining its oxygen content at least at 4ppm and then subjected to the treatment with the ion exchange resins.

5 Claims, No Drawings

PURIFICATION OF AN AQUEOUS SOLUTION OF ACRYLAMIDE

FIELD OF THE INVENTION:

The present invention relates to a process for the purification of an aqueous solution of acrylamide which comprises distilling off unreacted acrylonitrile and a part of the water, substantially in the absence of oxygen, from an aqueous solution of acrylamide which has been obtained by reacting in the liquid phase acrylonitrile with water in the presence of a coppercontaining catalyst which contains metallic copper and/or copper compounds in an amount within the range of 1–1000ppm calculated as copper, and thereafter treating the aqueous solution with ion exchange resins to prepare an aqueous solution of monomeric acrylamide suitable for the production of polyacrylamide.

BACKGROUND OF THE INVENTION

Acrylamide finds a wide variety of uses such as paper strengthening agent, coagulating or precipitating agent, and soil reforming agent. In recent years, it became possible to produce acrylamide in a comparatively easy manner according to a process wherein acrylonitrile is directly hydrated in the presence of a catalyst composed predominantly of metallic copper is place of the sulfuric acid method hitherto adopted.

In the above process wherein acrylonitrile is reacted with water in the presence of a copper-containing catalyst, the means disclosed, for example, in U.S. Pat. No. 3,642,894 for conducting the reaction while preventing the catalyst from contact with oxygen is generally employed to maintain the catalytic activity at a high level and to avoid side reactions.

This reaction is also disclosed, for example, in U.S. Pat. No. 3,911,009 which teaches a method with parameters for controlling the conversion rate of acrylonitrile to acrylamide at, for example, about 70%, and with the recovery of unreacted acrylonitrile by distillation or the like for re-use. The patent claims the method to be advantageous as a process for producing acrylamide on an industrial scale.

Means for recovering unreacted acrylonitrile from the reaction liquid obtained by the above mentioned general direct hydration process are known. For example, Japanese patent Prov. Publn. No. 7219/74 discloses a method wherein the reaction liquid is brought into contact with oxygen or an oxygen-containing gas to stabilize the acrylamide and thereafter water and acrylonitrile are evaporated off, leaving an aqueous solution of acrylamide having concentration of, for example, 30–50% by weight. Another known means for recovering acrylonitrile is disclosed in Japanese patent Prov. Publn. No. 36616/74 wherein the acrylonitrile and some water are distilled off in a non-oxidative atmosphere from the reaction liquid.

It has now been found that when the process wherein acrylonitrile and a part of the water are distilled off in a non-oxidative atmosphere from the reaction liquid is properly controlled, such process may be used to prevent satisfactorily the polymerization of the acrylamide, thus affording an easier operation than the process entailing the contact of the reaction liquid with oxygen or an oxygen-containing gas prior to distilling off the acrylonitrile.

The present invention relates therefore to an improvement in the known methods, the improved process comprising reacting acrylonitrile with water in the presence of a copper-containing catalyst while preventing the catalyst from contact with oxygen, distilling off unreacted acrylonitrile and a part of the water in a non-oxidative atmosphere from the reaction liquid to obtain an aqueous solution of acrylamide having a concentration of, for example, 30–50% by weight, and thereafter removing the impurities existing in the liquid such as copper and the like by a dual treatment of the solution with ion exchange resins.

As a means for removing the impurities from the watersoluble acrylamide obtained according to a process available before the development of the direct hydration process, there is known, for example, from the disclosure in U.S. Pat. No. 2,865,960 the use of a cation exchange resin activated in acidic form and an anion exchange resin activated in basic form.

On the other hand, a method is disclosed in Japanese patent Prov. Publn. No. 82011/75 wherein only a specific strongly basic anion exchange resin is used, and another method is disclosed in Japanese patent Prov. Publn. No. 83323/75 wherein the purification of a crude aqueous solution of acrylamide, obtained by the direct hydration process, is carried out by passing it through mixed beds of a cation exchange resin and an anion exchange resin.

According to applicants' study, it has been found that when only the treatment with a strongly basic anion exchange resin is carried out, it is difficult to remove copper ions and amine compounds to such a degree as to inhibit the production of polyacrylamide. Therefore, the joint use of a strongly acidic cation exchange resin and an anion exchange resin is considered to be necessary. However, when an aqueous solution of acrylamide is first passed through a strongly basic anion exchange resin and then through a strongly acidic cation exchange resin, the pH value of the aqueous solution of the acrylamide after the treatment with the strongly basic anion exchange resin increases to about 10 so that the solution of acrylamide becomes reactive and tends to form impurities by hydrolyzing and polymerizing reactions. On the other hand, when the method is reversed and the aqueous solution of acrylamide is first passed through a strongly acidic cation exchange resin and then through a strongly basic exchange resin, the pH value of the solution of acrylamide, after the initial lowering to 3–4, is again raised to about 10 by passing the solution to the strongly basic anion exchange resin whereby the solution easily undergoes hydrolyzing and polymerizing reaction to form impurities.

In a method where the aqueous solution of acrylamide is passed through mixed beds of a cation exchange resin and an anion exchange resin, the pH value of the aqueous solution of acrylamide at the outlet from the beds is almost neutral.

However, denaturation of the aqueous solution of acrylamide cannot be avoided as long as a strongly basic anion exchange resin is used. During operation of the mixed beds, the ion exchange resins undergo strong a fluidizing action by gas or liquid, upon regeneration of the resins and at the time of forming the beds, thus necessitating classification or mixing of the resins. As a result, the operation becomes complicated and is accompanied by such drawbacks as a significant loss of resins by impingement, crush and/or abrasion.

The aforementioned reveals that an aqueous solution of crude acrylamide cannot be purified into an aqueous solution of substantially high quality acrylamide merely by using a strongly acidic cation exchange resin and/or a strongly basic anion exchange resin in the process wherein unreacted acrylonitrile and a part of the water are distilled off from the reaction liquid substantially in the absence of oxygen. Further, it is often observed that, according to known conventional methods, an aqueous solution of acrylamide purified by the treatment with ion exchange resins changes in nature with the lapse of time; for example, within a period of one week to several months, changes are noticeable in the polymerization rate of acrylamide for producing polyacrylamide and in the solubility characteristics of polyacrylamide in water.

SUMMARY OF THE INVENTION

It is an object of the present invention to provide an improved purification process for producing an aqueous solution of acrylamide suitable for the production of acrylamide polymers.

It is another object of the present invention to provide a purification process for producing an aqueous solution of acrylamide which gives no change with the lapse of time in the polymerization rate of acrylamide in the production of acrylamide polymers and in the molecular weight and solubility in water of the resultant acrylamide polymers.

In accordance with the present invention, there is provided a process for the purification of an aqueous solution of acrylamide which comprises distilling off unreacted acrylonitrile and a part of the water, substantially in the absence of oxygen, from an aqueous solution of crude acrylamide which has been obtained by reacting acrylonitrile with water in the presence of a copper-containing catalyst which contains metallic copper and/or copper compounds in an amount within the range of 1–1000ppm calculated as copper, and thereafter treating the aqueous solution of acrylamide with ion exchange resins for purification. One of the features characterizing the invention resides in that the aqueous solution of acrylamide is first brought into contact with oxygen or an oxygen-containing gas and thereafter it is subjected to a dual treatment first with a strongly acidic cation exchange resin and then with a weakly basic anion exchange resin.

In accordance with a preferred embodiment of the present invention, the aqueous solution of acrylamide is brought into contact with oxygen or an oxygen-containing gas so as to maintain the concentration of the dissolved oxygen at least at 4ppm, and the oxygen treatment is carried out at a temperature within the range of 0°–70° C and under a pressure within the range of b 0.3–20kg/cm$^2$.

DESCRIPTION OF THE PREFERRED EMBODIMENTS:

An aqueous solution of acrylamide obtained by reacting in the liquid phase acrylonitrile with water in the presence of a copper-containing catalyst usually contains (1) unreacted acrylonitrile, (2) ions of metals such as copper as well as copper complex ions such as copper amine complex ions originated from the catalyst component, (3) impurities contained in the starting acrylonitrile, such as acetonitrile, and (4) by-products such as organic acids, for example, acrylic acid.

Among these impurities, unreacted acrylonitrile can easily be removed by conventional methods such as distillation. Copper in the copper ions and copper complex ions can also be removed easily, for example, by treatment with a strongly acid cation exchange resin in free form or in ammonium salt form.

However, organic substances in the copper complex ions, residual amounts of by-products, as well as the impurities contained in the starting acrylonitrile cannot satisfactorily be removed by a mere use of strongly acidic cation exchange resin. It is difficult to obtain polyacrylamide which is excellent in coagulating activity and solubility and suffers no change with the lapse of time by using an aqueous solution of acrylamide which contains these impurities.

In contrast, no change with lapse of time is found in the properties of an aqueous solution of acrylamide purified according to the process of this invention and in the properties of polyacrylamide obtained from an aqueous solution of the purified acrylamide.

The reason why the above mentioned remarkable effects can be achieved by the process of this invention is still unclear. It is surmised, however, that very small amount of various substances formed during the direct hydration of acrylonitrile in the presence of a copper-containing catalyst are denatured and rendered easily adsorbable by a proper treatment with ion exchange resins and that the above mentioned shelt-life change in properties of the acrylamide aqueous solution and of the polyacrylamide is prevented by the removal of the various impurity substances by adsorption.

It is generally observed that very fine particles of metallic copper and/or copper compounds originated from the coppercontaining catalyst are present in very small amount in the treated reaction liquid. It is extremely difficult by an ordinary filtering operation to remove such very fine particles to the desired low levels. For example, an aqueous solution of purified acrylamide passed through columns of the ion exchange resins is sometimes contaminated with such very fine particles in an amount of about 1ppm, which usually shows a tendency to degrade the quality of the aqueous solution of purified acrylamide. This undesirable degradation phenomenon, however, when the process of this invention is carried out, is not observed at all and, moreover, the equally undesirable phenomenon of polymerization of acrylamide often occurring during the course of treatment with the ion exchange resins is also not observed.

In the process of this invention, cuprous ion ($Cu^+$) existing in the aqueous solution of acrylamide is oxidized to cupric ion ($Cu^{++}$) by the treatment with oxygen. Although the ion equivalent in the treatment with the ion exchange resin is thus increased, no reduction is found in the running ion exchange capacity under ordinary operation conditions for the column of the cation exchange resin, for example, at a flow rate of about 2–20$l$/hr in terms of SV and a tendency of a rather slight increase in the capacity is found in certain cases.

Examples of the copper-containing catalysts utilizable in the process of this invention are (1) metallic copper in the form of wire or powder and a copper ion, (2) reduced copper obtained by reducing a copper compound such as cupric oxide, cupric hydroxide or a copper salt at a high temperature of 100°–400° C with hydrogen or carbon monoxide, (3) reduced copper obtained by reducing in the liquid phase a copper compound such as cupric oxide, cupric hydroxide or a copper salt with a reducing agent such as hydrazine, an alkali metal or alkali earth metal borohydride or formaldehyde, (4) reduced copper obtained by treating in the liquid phase a copper compound such as cupric oxide, cupric hydroxide or a copper salt with a metal which is larger in ionizing tendency than copper, such as zinc, aluminum, iron or tin, (5) Raney copper obtained by developing a Raney alloy composed of aluminum, zinc or magnesium and copper, (6) metallic copper obtained by pyrolysis of an organocopper compound such as cupric formate or cupric oxalate at a temperature ranging, for example, from 100° C to 400° C, and (7) a pyrolyzed product of copper hydride. These copper-containing catalyst may contain chromium, molybdenum or a like metal usually used other than copper in addition to conventional supports.

An aqueous solution of acrylamide to which the purification process of this invention can be applied is obtained by reacting acrylonitrile with water in an almost freely determined amount, i.e. in an amount 2–50 times the stoichiometric amount needed for acrylonitrile at a reaction temperature of 20°–200° C, preferably 50°–150° C, in the presence of the above mentioned copper-containing catalyst. The reaction pressure employed is atmospheric pressure or superatmospheric pressure corresponding to the spontaneous vapor pressure at the reaction temperature used. The reaction is carried out batchwise or continuously under various conditions including fixed bed type contact or suspended bed type contact with the catalyst. In addition, this reaction is carried out in the liquid phase between the acrylonitrile and water in the presence of the copper-containing catalyst, while preventing the reactants from contact with oxygen or an oxygen-containing gas as far as possible.

The aqueous solution of acrylamide obtained according to such process usually contains 6–45% by weight of acrylamide as well as various impurities such as those mentioned above. Acrylonitrile and relatively course catalyst particles contained as impurities in the aqueous solution are usually removed by distillation, filtration and the like, prior to the treatment with the ion exchange resins.

The above reaction liquid is then subjected to an ordinary distillation operation with a view to distilling off unreacted acrylonitrile contained in the liquid and concentrating it to an aqueous solution of acrylamide having a concentration of, for example, 30–50% by weight.

When the operation is carried out with the concurrent prevention of contact between the reaction liquid and the oxygen or the oxygen-containing gas such operation may be conducted economically at temperatures of 50–120° C and pressures of 50 torr to 2 atms., although these ranges depend to some extent on the composition of the liquid.

In order to prevent the reaction liquid from contact with air, the equipment should be sealed or shielded with an inert gas such as nitrogen from the external air even in the case of equipment used under atmospheric pressure. In case a washing liquid from the equipment in other process steps is introduced into a distilling device for recovery, for example, said washing liquid should be prevented at all times from contact with the oxygen or the oxygen-containing gas.

In the process of this invention wherein unreacted acrylonitrile and a part of the water in the reaction liquid are distilled off substantially in the adsence of oxygen, the permissible amount of oxygen present in this case is usually at most 1/30, preferably at most 1/100 in weight ratio to the amount of cuprous ion, although the permissible amount of oxygen may vary according to the concentrations of acrylamide and cuprous ion in the liquid and according to the temperature of the liquid.

An aqueous solution of acrylamide to which the process of this invention is applicable is generally, by weight, 1–80%, preferably 5–60%, acrylamide and one containing metallic copper or copper compounds in an amount within the range of 1–1000ppm, more usually 5–600ppm calculated as copper. The copper compounds contained in the aqueous solution of acrylamide include copper oxides and copper hydroxides as well as ionic compounds such as copper salts.

The above mentioned aqueous solution of acrylamide is then brought into contact with oxygen or an oxygen-containing gas prior to the treatment with the ion exchange resins. Even if the amount of oxygen or oxygen-containing gas is small, a technical advantage is achieved.

To achieve satisfactory results, the concentration of oxygen dissolved in the aqueous solution of acrylamide is preferably maintained at least at 4ppm.

The reason why the concentration of oxygen dissolved in the aqueous solution of acrylamide should be maintained at least at 4ppm is that if any substance reactive with the dissolved oxygen is present in a relatively large amount, the oxygen often becomes quantitatively insufficient, so that the desired effect may not satisfactorily be achieved. As a further explanation, it is now understood that the reaction between the oxygen dissolved and substances reactive therewith, i.e. reactive substances composed of copper and/or copper compounds and other unknown substances, takes place over a relatively long period of time.

No special consideration is necessary with regard to the actual means for conducting the oxygen treatment in the process of this invention. Such oxygen treatment is readily attained by merely blowing oxygen or an oxygen-containing gas, such as nitrogen, into the aqueous solution or by mixing the solution with a liquid saturated with oxygen. A preferred concentration of oxygen in the aqueous solution is substantially a saturated concentration greater than 4ppm. An example of the preferred concentration is 8ppm of dissolved oxygen prepared by blowing oxygen into the aqueous solution under atmospheric pressure. however, if the concentration of oxygen dissolved in the aqueous solution is less than 4ppm, the oxygen treatment will be unsatisfactory in the results obtained. Typical process conditions for the oxygen treatment include a temperature range of 0–70° C, preferably 10–50° C and a pressure range of 0.3–20kg/cm², preferably 0.6–10kg/cm². The treating time is obviously influenced by the concentration of oxygen dissolved in the aqueous solution and by the temperature, but a treating time of 1 minute to 100 hours, preferably more than 10 minutes, more preferably 10 minutes to 10 hours is usually adequate.

The aqueous solution of acrylamide brought into contact with oxygen or an oxygen-containing gas having a concentration of oxygen dissolved in the aqueous solution of at least 4ppm, with or without being subjected to the oxygen treatment, is then subjected to the treatment with the ion exchange resins to remove impurities by adsorption.

According to the process of this invention, the aqueous solution acrylamide is purified by subjecting it to the treatment first with a strongly acidic cation exchange resin and then with a weakly basic anion exchange resin.

Strongly acidic cation exchange resins utilizable for the process of this invention may be selected from ordinary ones obtained by sulfonating styrene-divinylbenzene copolymer. Illustrative of such resin are, for example, Amberlite IR-120B (Rohm & Haas, U.S.A.), Lewatit SP-112 (Bayer, W. Germany) and Diaion PK212 (Mitsubishi Kasei Kogyo KK, Japan). The resin per se may be in gel form or in macroporous form. The counter ion in the exchange groups of the strongly acidic cation exchange resin is preferably in the H form, considering the rate of removing copper.

The pH value of the aqueous solution of acrylamide treated with the strongly acidic cation exchange resin is lowered usually to 3.5–4.0. Accordingly, the aqueous solution of acrylamide tends to polymerize in the neighborhood of the outlet of the apparatus for treatment with the strongly acid cation exchange resin and the inlet of the apparatus for treatment with the weakly basic anion exchange resin. In such case, polymerization of acrylamide can be prevented by optimizing the resin treatment conditions as follows:

Polymerization of acrylamide may be prevented by (a) coating the treating facilities coming into contact with the aqueous solution of acrylamide during the purification process, especially the area of the fixed bed column, with a synthetic resin such as a phenol resin, polyethylene, polypropylene or polyvinyl chloride, of (b) controlling the flow rate of the aqueous solution running through the fixed bed column to a range of 2–20m/h in terms of line velocity.

The flow of the aqueous solution of acrylamide introduced into the fixed type column of the ion exchange resin may be either ascending or descending. The temperature of the flowing liquid is within the range of 5°–50° C, preferably 10°–30° C in view of the stability of the aqueous solution of acrylamide. Deactivated ion exchange resins are regenerated according to conventional methods.

The aqueous solution of acrylamide after treatment with the strongly acidic cation exchange resin is then treated with a weakly basic anion exchange resin.

Weakly basic anion exchange resins utilizable for the process of this invention are generally prepared by chloromethylating styrenedivinylbenzene copolymer and then aminating the chloromethylated copolymer with a primary or secondary amine. The exchange groups can be selected from ordinary ones carrying a primary, secondary or tertiary amino group. Illustrative of the weakly basic anion exchange resin are, for example, Amberlite IRA-93 (Rohm & Haas, U.S.A.), Lewatit MP62 (Bayer, W. Germany) and Diaion WA10 (Mitsubishi Kasei Kogyo KK, Japan). The resin per se may be in gel form or in macroporous form. The counter ion in the exchange groups of the weakly basic anion exchange resin is preferably in the OH form.

The conditions for the ion exchange treatment with the weakly basic anion exchange resin are almost the same as those employed with the strongly acidic cation exchange resin.

The process of this invention involves the dual treatment with the strongly acidic cation exchange resin followed by the weakly basic anion exchange resin as one of the indispensable conditions. Failing this, the results lead to an aqueous solution of acrylamide having a pH value as high as 9–11 and with a tendency to form impurities and to be denatured. As stated above, the process of this invention does not permit the formation of impurities as seen when treating an aqueous solution of acrylamide with an anion exchange resin and then with a cation exchange resin. In addition, the process of this invention is devoid of the disadvantages encountered when using mixed beds of ion exchange resins, such as formation of impurities, loss of ion exchange resins on regeneration and at the time of forming the mixed beds and complications in operations.

The aqueous solution of the present invention has an almost neutral pH value after treatment with the weakly basic anion exchange resin, and impurities contained in the solution, which may deteriorate the quality of polyacrylamide, can be eliminated to such an extent that the properties of the polyacrylamide are for all practical purposes not affected.

As it has been described in detail, the overall process of the present invention comprises reacting in the liquid phase acrylonitrile with water in the presence of a copper-containing catalyst, distilling off unreacted acrylonitrile and some water substantially in the absence of oxygen, treating the reaction liquid with oxygen or an oxygen-containing gas with the concentration of the dissolved oxygen maintained at least at 4ppm, and further treating it with a strongly acidic cation exchange resin and then with a weakly basic anion exchange resin. As a modification, a treatment of the reaction liquid with a strongly acidic cation exchange resin may be had before the treatment with oxygen or an oxygen-containing gas, after which there follows the dual treatment with a strongly acidic cation exchange resin and then with a weakly basic anion exchange resin.

EXAMPLE 1

To a suspended bed reactor using Raney copper as catalyst were continuously supplied previously deoxygenated acrylonitrile and deoxygenated pure water. The resulting reaction liquid was transferred to a catalyst filter (2000 mesh stainless steel nets were used as filter) directly connected to be reactor, where the reaction liquid was filtered. The filtrate was transferred to a distillation tower connected directly to the catalyst filter and operated under reduced pressure, where almost all of unreacted acrylonitrile and a part of water were distilled off to obtain an aqueous solution of acrylamide having a concentration of 33% by weight as bottoms of the distillation tower. Analysis of this aqueous solution (referred to hereinafter simply as "crude aqueous solution") showed that the amount of remaining acrylonitrile was less than 0.1% and the concentration of copper was 120ppm.

This experiment was continued for 3 weeks and the crude aqueous solution obtained was placed in a series of 200 liter containers where the solution was treated for 3 hours by blowing air thereinto at ordinary temperature under atmospheric pressure. During and after the treatment, the concentration of oxygen dissolved in the crude aqueous solution was about 8ppm. A glass ion exchange column of 20mm in inner diameter and 1 meter in length was packed with 200ml of Amberlite IR-120B (Rohm & Hass, U.S.A.) as strongly acidic cation exchange resin and this ion exchange resin was regenerated in the H form. A column similar in size to the above mentioned was packed with 200ml of Lawatit MP-62 (Bayer, W. Germany) as weakly basic anion exchange resin and this ion exchange resin was kept in free form (OH form). This column was connected directly to the exit of the cation exchange column. The crude aqueous solution subjected to the oxygen treatment was then passed through the columns at a flow rate of 1 liter/hr. As the effluent had a pH value varying within the range of 3–8, hydrochloric acid or caustic soda were occasionally added to the effluent to adjust the pH value to 7.0 or thereabout. (The pH-adjusted liquid will be referred to hereinafter as "purified liquid").

The purified liquid obtained by passing the crude aqueous solution through the ion exchange columns for 4 days had a copper concentration of 0.05ppm or less.

The next day, after completion of the ion exchange treatment, this purified liquid was subjected to polymerization conducted adiabatically in the presence of a mixed redox catalyst composed of ammonium persulfate and sodium bisulfite. The polymerization time was 50 minutes. After the polymerization temperature reached the maximum temperature, the vessel accomodating the polymer was transferred into a water bath kept at 90° C, allowed to stand stationarily for 2 hours and then cooled. The resultant contents were thinly cut, taken up in methanol, pulverized, dehydrated and then dried under reduced pressure at 50° C for 1 hour whereby powdery polyacrylamide was obtained.

This polymer was easily soluble in water at ordinary temperature and was found to have a molecular weight of 10,300,000 when measured according to the viscosity method. No polymer was detected when the columns used for the ion exchange treatment were checked.

The purified liquid was stored for 30 days at ordinary temperature and then subjected to a similar polymerization test. The polymerization time in this case was 56 minutes. The polymerization product was treated in the same manner as described above. The resultant polymer had good solubility in water and a molecular weight of 10,800,000 and was found almost the same in quality as the polymer produced from the unstored purified liquid.

EXAMPLE 2

The same experiment as described in Example 1 was carried out except that a equivolum mixture of air and nitrogen (ratio 1:1) was used in place of air. During and after the treatment with the mixture of gases, the concentration of oxygen dissolved in the crude aqueous solution was about 4ppm, while the concentration of copper in the purified liquid was less than 0.05ppm. The next day, after completion of the ion exchange treatment, the purified liquid was subjected to polymerization (polymerization time 62 minutes). The resultant polymer had good solubility in water and a molecular weight of 11. No polymer was detected when the columns used for the ion exchange treatment were checked. The purified liquid stored for 30 days was also subjected to polymerization (polymerization time 60 minutes). The resultant polymer had good solubility in water and a molecular weight of 10,500,000 and was found almost the same in quality as the polymer produced from the unstored purified liquid.

COMPARATIVE EXAMPLE 1

The same experiment as described in Example 1 was carried out except that the oxygen treatment was omitted. The crude aqueous solution discharged from the distillation tower was immediately supplied to the columns for cation and anion exchange treatments while preventing the solution from contact with oxygen. The resultant liquid was then ph-adjusted in the open air to obtain a purified liquid. The concentration of oxygen dissolved in the crude aqueous solution was less than 0.2ppm, while the concentration of copper in the purified liquid was within a range of 1–3ppm during the 4-day ion exchange treatment and was far beyond the value desirable in the product. When the columns used for the cation and anion exchange treatments were checked, a large amount of a polymer in popcorn form was observed in both columns. It was assumed therefore that the columns would have clogged if used continuously for prolonged period of time.

COMPARATIVE EXAMPLE 2

In order to remove residual copper which could not be eliminated in Comparative Example 1, a porous porcelain filter was equipped in front of the ion exchange column. When the same experiment as described in Comparative Example 1 was carried out, the porcelain filter was clogged in about 1 day. The concentration of copper in the resulting purified liquid was about 0.05ppm. The polymerization time was 70 minutes. The resultant polymer had good solubility in water and a molecular weight of 9. The purified liquid stored for 30 days was also subjected to polymerization (polymerization time 4 hours and 55 minutes). The resultant polymer showed unsatisfactory solubility in water and was considerably denatured. An insoluble portion of the polymer reached about ⅓ of the polymer.

COMPARATIVE EXAMPLE 3

The ion exchange treatment was carried out in the same manner as described in Example 1 except that Diaion PA316 (strongly basic) was used as the anion exchange resin in the OH form in place of Lewatit MP-62 of Example 1 (weakly basic) anion exchange resin. The pH value of the resultant aqueous solution of acrylamide was 9.5.

EXAMPLE 3

One more cation exchange column was added in the operation of Example 1. A glass ion exchange column of 20mm in inner diameter and 1 in meter length was packed with 200ml of Amberlite IR-120B (Rohm & Haas, U.S.A.) as strongly acidic cation exchange resin and this ion exchange resin was regenerated in the H form. A crude aqueous solution obtained in the same manner as described in Example 1 was passed through this column at a flow rate of 1 liter/hr. The effluent was then subjected to the air treatment, the cation exchange treatment, the anion exchange treatment, and the pH-adjustment conducted in the same manner as described in Example 1. The purified liquid obtained after a 2-day ion exchange treatment had a copper concentration of 0.05ppm or less. The next day, the purified liquid was subjected to polymerization (polymerization time 55 minutes). The resultant polymer had good solubility in water and a molecular weight of 9,600,000. The purified liquid stored for 30 days was also subjected to polymerization (polymerization time 51 minutes). The resultant polymer had good solubility in water and a molecular weight of 9,900,000 and was found almost the same in quality as the polymer produced from the unstored purified liquid.

What is claimed is:

1. In the purification of acrylamide aqueous solutions obtained in a process which comprises reacting in the liquid phase acrylonitrile with water in the presence of a copper-containing catalyst which contains 1–1000ppm of metallic copper, distilling off from the thus obtained crude solution unreacted acrylonitrile and a part of the water substantially in the absence of oxygen, and thereafter purifying the resultant aqueous solution by means of ion exchange resin treatment, the improvement which comprises contacting said crude aqueous solution of acrylamide with a gas selected from the group consisting of oxygen and oxygen-containing gases, the amount of the oxygen dissolved in the solution being at least 4ppm, and thereafter subjecting the aqueous solution to a dual treatment first with a strongly acidic cation exchange resin and then with a weakly basic anion exchange resin.

2. The improvement according to claim 1 wherein the concentration of the oxygen dissolved in said aqueous solution is about 8ppm.

3. The improvement according to claim 1 wherein said dual treatment is carried out at temperatures within the range of 0°–70° C and pressures within the range of 0.3–20kg/cm$^2$.

4. The improvement according to claim 1 wherein the time required for said oxygen treatment is at least 10 minutes.

5. The improvement according to claim 1, further comprising a pre-treatment of the aqueous crude solution of acrylamide with a strongly acidic cation exchange resin prior to said contact with said selected gas.